United States Patent
Yoon

[11] Patent Number: 5,984,938
[45] Date of Patent: *Nov. 16, 1999

[54] SURGICAL INSTRUMENT WITH JAWS AND MOVABLE INTERNAL SCISSORS AND METHOD FOR USE THEREOF

[76] Inventor: InBae Yoon, 2101 Highland Ridge Dr., Phoenix, Md. 21131

[*] Notice: This patent is subject to a terminal disclaimer.

[21] Appl. No.: 08/847,187

[22] Filed: May 1, 1997

Related U.S. Application Data

[63] Continuation-in-part of application No. 08/376,186, Jan. 20, 1995, Pat. No. 5,665,100, which is a continuation-in-part of application No. 08/281,814, Jul. 28, 1994, abandoned, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.⁶ .................................................. A61B 17/32
[52] U.S. Cl. ........................ 606/170; 606/205; 606/139; 606/144
[58] Field of Search ................................. 606/205, 207, 606/151, 170, 142, 144, 139, 149, 148, 167

[56] References Cited

U.S. PATENT DOCUMENTS

| | | |
|---|---|---|
| 2,002,594 | 3/1935 | Wappler et al. . |
| 2,004,559 | 11/1935 | Wappler et al. . |
| 2,028,635 | 9/1936 | Wappler . |
| 4,077,412 | 3/1978 | Moossun . |
| 4,103,680 | 8/1978 | Yoon . |
| 4,174,715 | 11/1979 | Hasson . |
| 4,249,533 | 2/1981 | Komiya . |
| 4,257,420 | 3/1981 | Terayama . |
| 4,372,295 | 2/1983 | Heckele . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,557,255 | 12/1985 | Goodman . |
| 4,598,699 | 7/1986 | Garren et al. . |
| 4,788,966 | 12/1988 | Yoon . |
| 4,869,268 | 9/1989 | Yoon . |
| 4,966,583 | 10/1990 | Debbas . |
| 5,025,778 | 6/1991 | Silverstein et al. . |
| 5,037,433 | 8/1991 | Wilk et al. . |
| 5,139,487 | 8/1992 | Baber . |
| 5,147,373 | 9/1992 | Ferzli . |
| 5,176,695 | 1/1993 | Dulebohn . |
| 5,190,541 | 3/1993 | Abele et al. . |
| 5,211,650 | 5/1993 | Noda . |
| 5,217,460 | 6/1993 | Knoepfler . |
| 5,226,908 | 7/1993 | Yoon . |
| 5,234,443 | 8/1993 | Phan et al. . |
| 5,261,917 | 11/1993 | Hasson et al. . |
| 5,312,391 | 5/1994 | Wilk . |

(List continued on next page.)

*Primary Examiner*—Michael Buiz
*Assistant Examiner*—Daphna Shai
*Attorney, Agent, or Firm*—Blank Rome Comisky & McCauley LLP

[57] ABSTRACT

A surgical instrument includes a forceps unit for being positioned within an anatomical cavity and inner member having scissors at a distal end thereof. The forceps unit includes a housing, an outer tubular member, an intermediate member, and a handle mechanism coupled with at least one of the intermediate and outer tubular members for creating relative movement between the intermediate and outer tubular members. The outer tubular member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The inner member includes a tubular member removably disposed at least partly within the intermediate member and carrying scissors for performing at least one of the functions of cutting, cauterizing, or the like. The scissors can be selectively advanced to be between the jaws for cutting by closing the jaws.

25 Claims, 10 Drawing Sheets

U.S. PATENT DOCUMENTS

| | | |
|---|---|---|
| 5,318,589 | 6/1994 | Lichtman . |
| 5,324,254 | 6/1994 | Phillips . |
| 5,336,231 | 8/1994 | Adair . |
| 5,348,555 | 9/1994 | Zinnanti . |
| 5,366,476 | 11/1994 | Noda . |
| 5,398,670 | 3/1995 | Ortiz et al. . |
| 5,403,332 | 4/1995 | Christoudias . |
| 5,462,561 | 10/1995 | Voda . |
| 5,462,562 | 10/1995 | Elkus . |
| 5,476,505 | 12/1995 | Limon . |
| 5,496,310 | 3/1996 | Exconde et al. . |
| 5,538,008 | 7/1996 | Crowe . |
| 5,542,949 | 8/1996 | Yoon . |
| 5,549,623 | 8/1996 | Sharpe et al. . |
| 5,562,102 | 10/1996 | Taylor . |
| 5,569,241 | 10/1996 | Edwards . |
| 5,578,007 | 11/1996 | Imran . |
| 5,607,435 | 3/1997 | Sachdeva et al. . |
| 5,611,813 | 3/1997 | Lichtman . |
| 5,620,459 | 4/1997 | Lichtman . |
| 5,746,770 | 5/1998 | Zeitels et al. . |
| 5,766,169 | 6/1998 | Fritzsch et al. . |

SURGICAL INSTRUMENT WITH JAWS AND MOVABLE INTERNAL SCISSORS AND METHOD FOR USE THEREOF

CROSS-REFERENCE TO RELATED APPLICATIONS

This application is a continuation-in-part of Ser. No. 08/376,186, filed on Jan. 20, 1995, now U.S. Pat. No. 5,665,100 which is a continuation-in-part of applicant's patent application Ser. No. 08/281,814, filed Jul. 28, 1994, abandoned which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention:

The present invention relates generally to medical procedures and instruments and, more particularly, to a multifunctional instrument having jaws, a central channel formed through the jaws, and a moveable inner member having scissors disposed in the channel.

2. Discussion of the Related Art:

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts. Also, it is often desirable to manipulate tissue, prior to cutting the tissue or performing other procedures, with a single instrument. Conventional devices do not facilitate such procedures.

SUMMARY OF THE INVENTION

Accordingly, it is a primary object of the present invention to overcome the above mentioned disadvantages of the prior art with an endoscopic instrument capable of performing multiple functions.

Another object of the present invention is to minimize the number of incisions required for performing an endoscopic procedure by performing grasping, manipulating, cutting and other functions through a single incision with an endoscopic instrument having a forceps unit with jaws for performing grasping functions and a movable hollow inner member disposed in a central channel and having scissors that can be inserted in the jaws for performing cutting, dissecting, creating suction, and cauterizing through the forceps unit.

A further object of the present invention is to reduce the need for frequent substitution of instruments through a single incision by carrying out multiple functions with a single endoscopic instrument having a forceps unit that remains within an anatomical cavity and a moveable scissors member that can be selectively withdrawn or advanced into the forceps jaws.

It is another object of the present invention to lock jaws of an endoscopic instrument together to ensure smooth entry of the endoscopic instrument through a portal sleeve and to prevent inadvertent snagging of anatomical tissue and to permit the same linkage to be used for closing jaws for grasping or for cutting with the scissors.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and a scissors member is facilitated, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity and a moveable inner member having scissors disposed in the forceps unit. The forceps unit includes a housing, an outer tubular member, an intermediate member, and a handle mechanism coupled with at least one of the intermediate and outer tubular members for creating relative movement therebetween. The outer tubular member has a proximal end mounted on the housing and terminates distally at a distal end. The intermediate member has a tubular body disposed telescopically within the outer tubular member, a proximal end mounted in the housing and an integral one-piece distal end defining a pair of opposed jaws resiliently biased apart such that relative movement of the outer tubular member distal end over the jaws causes the jaws to close. The inner member includes a hollow shaft slidingly disposed at least partly within a central channel formed in the intermediate member and scissors mounted on a distal end of the shaft for performing at least one of the functions of cutting, creating suction, aspirating, irrigating and cauterizing.

A further aspect of the present invention is generally characterized in a method of performing an endoscopic procedure including the steps of introducing a tubular member with integral one-piece jaws through an opening in an anatomical cavity wall, grasping anatomical tissue with the jaws releasing the tissue, advancing a hollow moveable inner member having scissors distally through the tubular member, and performing at least one of cutting, grasping, dissecting, cauterizing, irrigating and aspirating with the inner member.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

The endoscopic instrument of the present invention can be utilized in any type of anatomical cavity. Accordingly, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
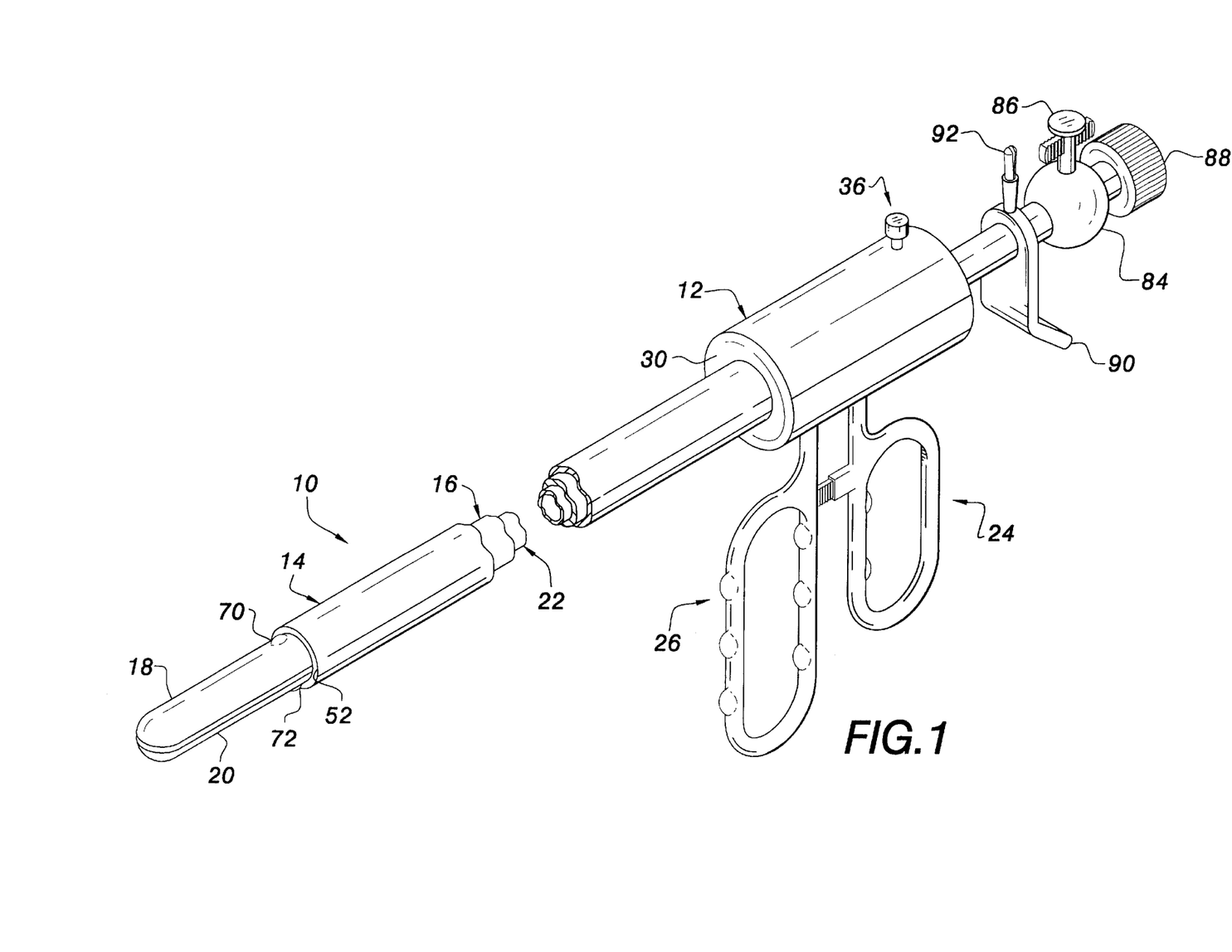
FIG. 1 is a perspective view, broken longitudinally, of an endoscopic instrument according to the present invention.

Endoscopic instrument 10 according to a preferred embodiment of the present invention, as shown in FIG. 1, includes housing 12, tubular outer member 14 extending distally from the housing 12, tubular intermediate member 16 telescopically fitted within outer member 14 and having opposed jaws 18 and 20 on a distal end thereof, fixed handle 24 and moveable handle 26 extending from the housing at an angle relative to the longitudinal axis of the instrument, and inner member 22 which is at least partly telescopically fitted within intermediate tubular member 16.

Figure 2:
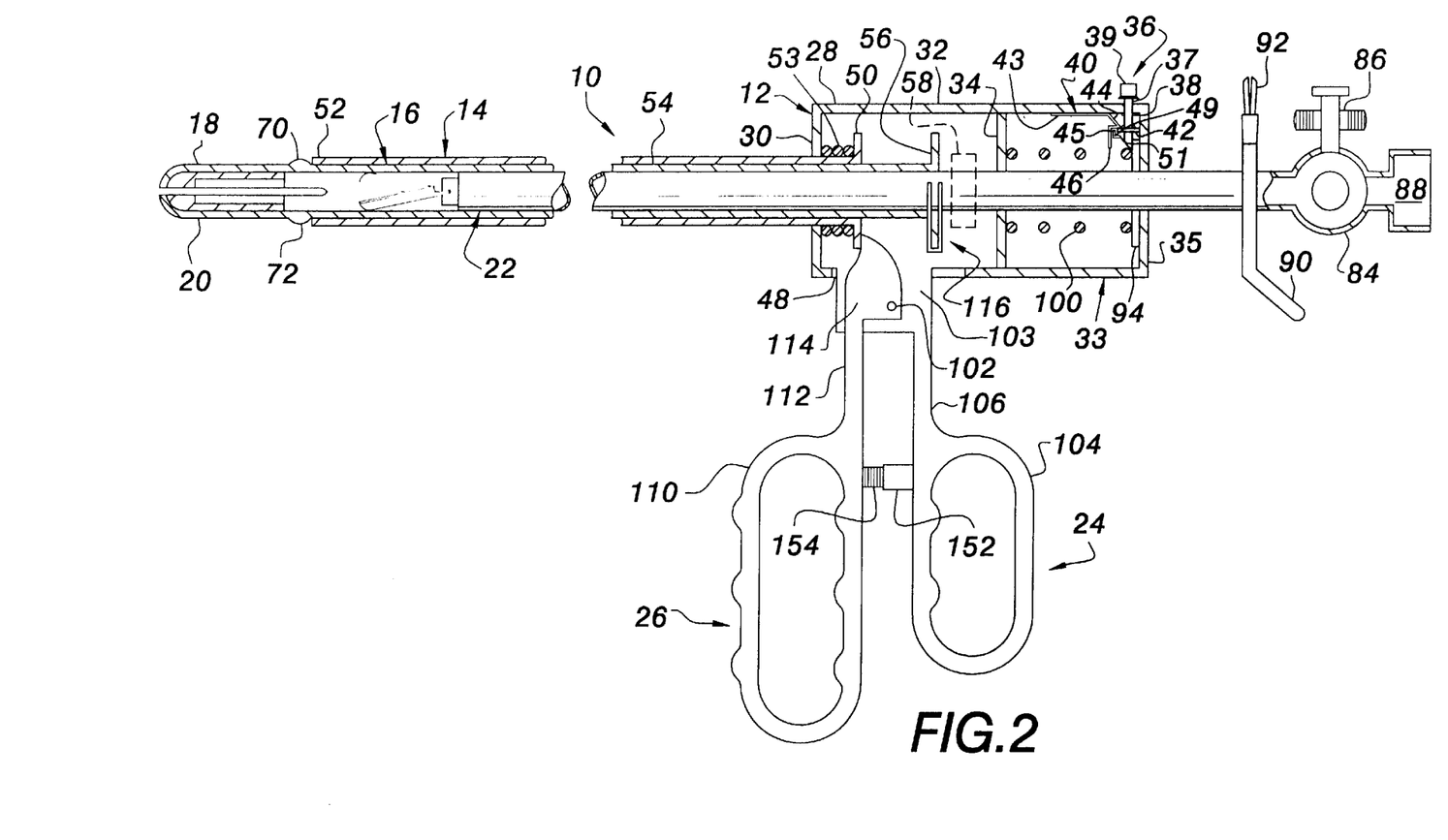
FIG. 2 is a sectional view of the preferred embodiment.

As illustrated in FIG. 2, housing 12 is generally tubular with cylindrical sidewall 28 and front and rear walls 30 and 31 closing opposite ends of the cylindrical sidewall 28. Intermediate wall 34 divides housing 12 into two chambers. Slotted opening 48 is formed in cylindrical a sidewall 28 of housing 12 and extends longitudinally between front wall 30 and intermediate wall 34 of housing 12 to permit movable handle 26 to pass therethrough. Fixed handle 24 extends from plate 103 fixed to a portion of housing 12 proximate slot 48. Plate 103 can be formed integrally with housing 12 or can be fixedly attached to housing 12 to be stationary relative thereto. Movable handle 26 is pivotably mounted to plate 103 by pin 102.

Outer member 14 is open at both ends and extends through an opening in front wall 30 to terminate proximally at transverse flange 50 disposed between front wall 30 and intermediate wall 34 of housing 12. Distal end 52 of outer member 14 can be blunt as shown, tapered, beveled or chamfered as desired or have any other suitable distal configuration. Preferably, outer member 14 is made of a substantially cylindrical length of a substantially rigid material, such as stainless steel or other medically acceptable plastic or metal material.

Figure 3:
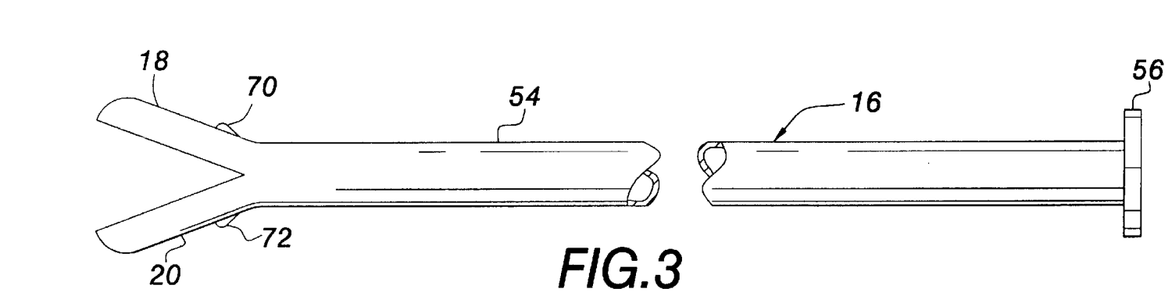
FIG. 3 illustrates the intermediate member of the preferred embodiment removed from the outer member for illustrative purposes.
Figure 4:
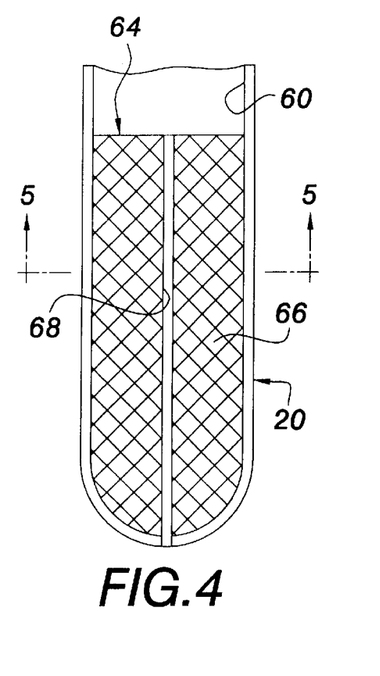
FIG. 4 illustrates one of the jaws of the preferred embodiment.
Figure 5:
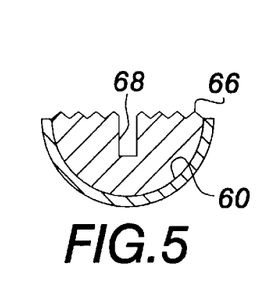
FIG. 5 illustrates the jaw of FIG. 4 in section along line 5—5.
Figure 6:
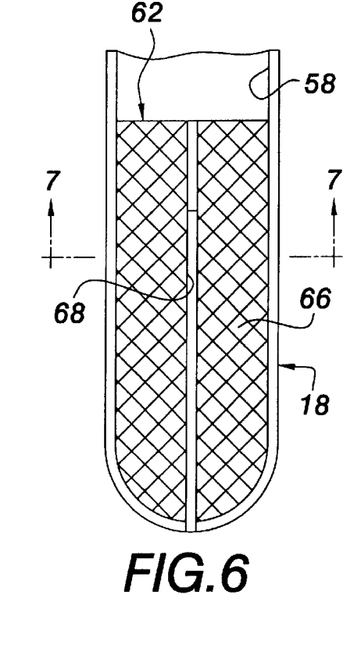
FIG. 6 illustrates the other jaw of the preferred embodiment.
Figure 7:
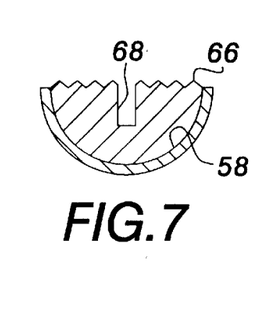
FIG. 7 illustrates the jaw of FIG. 6 in section along line 7—7.

Intermediate member 16 includes tubular body 54 telescopically fitted within outer member 14. Tubular body 54 terminates proximally at transverse flange 56 disposed within housing 12 between flange 50 and intermediate wall 34; and, as best seen in FIGS. 3 which shows intermediate member 16 removed from outer member 14 for illustrative purposes, a distal end of tubular body 54 is split longitudinally to form integral one-piece jaws 18 and 20 that oppose one another. Jaws 18 and 20 are normally biased apart as shown and define opposed semicylindrical recesses 58 and 60 for carrying jaw inserts 62 and 64 (see FIGS. 5 and 7). Jaw inserts 62 and 64 can be permanently or removably secured within semicylindrical recesses 58 and 60 respectively using adhesives, detents, or any other suitable method of attachment or can be formed with jaws 18 and 20 as an integral one-piece construction.

Each of jaw inserts 62 and 64 defines a grasping surface or tread 66 suitable for grasping anatomical tissue, or holding instruments such as a needle, and a longitudinal slot or groove 68 extending from a proximal end of the insert to a position proximally spaced from the distal end of the insert. A repeated pattern of diamond-shaped protrusions is shown for tread 66. However, other surfaces such as those having parallel ribs or textured portions could be used. The length, width and depth of each groove 68 will depend on the size of a scissors carried by the inner member 22 as will be described in more detail below. Wedge-like cams 70 and 72 are formed on respective exterior surfaces of jaws 18 and 20 and are distally spaced from outer member distal end 52 when jaws 18 and 20 are entirely open. Cams 70 and 72 taper toward the joint region or junction where each jaw connects with tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing upper and lower jaws 18 and 20 apart while permitting jaws 18 and 20 to be moved elastically towards one another in response to axial forces acting on jaws 18 and 20. Referring again to FIG. 2, it can be seen that bias member 53 is connected between flange 50 and front wall 30 such that outer member 14 is normally biased in a proximal direction relative to intermediate member 16. Bias member 53 is shown as a helical coil spring disposed around intermediate member 16 and held in compression between the outer member flange 50 and front wall 30. However, bias member 53 can be constituted of various other types of springs as well as other types of bias devices including tension springs, torsion springs, pan springs, leaf springs, rubber, plastic or magnets, for example.

Figure 8:
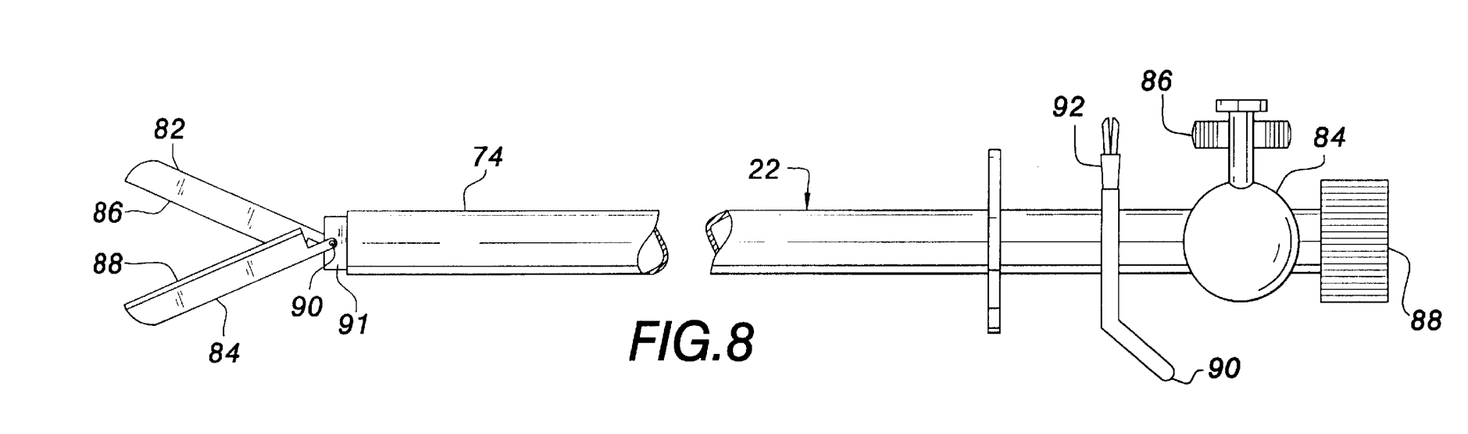
FIG. 8 illustrates the inner member removed from the intermediate mem6er and the outer member for illustrative purposes.
Figure 9:
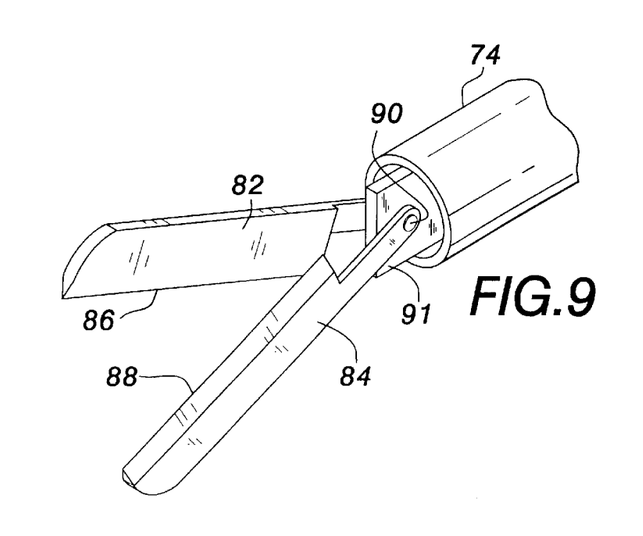
FIG. 9 illustrates the distal end of the inner member.
Figure 15:
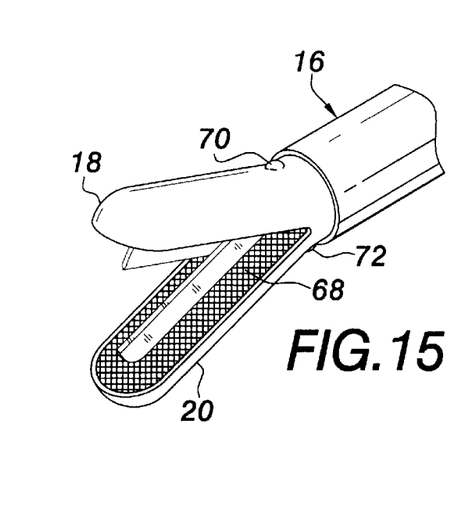
FIG. 15 illustrates the jaws with the inner member advanced to place the scissors therein.

As best seen in FIGS. 8 and 9 which illustrate inner member 22 removed from outer member 14 and intermediate member 16 for illustrative purposes, inner member 22 includes a cylindrical or tubular shaft 74 and an operating member in the form of a pair of pivoted scissor blades 82 and 84. Scissor blades 82 and 84 are configured to fit respectively within grooves 68 in movable jaws 18 and 20 as shown in FIG. 15 and include opposed cutting edges 86 and 88. Proximal ends of scissor blades 82 and 84 are pivotally mounted on pin 90 secured to flat base 91 extending distally from tubular shaft 74. Base 91 extends diametrically across an opening in the distal end of tubular shaft 74. Scissor blades 82 and 84 are biased apart with a bias member such as a torsion spring (not shown) disposed around pin 90 and connected between scissor blades 82 and 84. Inner member 22 can be advanced through intermediate member 16 so that scissor blades 82 and 84 slide into grooves 68. With scissor blades 82 and 84 seated within grooves 68, cutting is accomplished by opening and closing jaws 18 and 20 in the manner described below.

Cutting edges 86 and 88 of scissor blades 82 and 84 slidingly contact one another to cut anatomical tissue held therebetween or can be directly aligned to perform a chopping-type cut. If tubular shaft 74 is open at a distal end, fluids can be introduced or drawn out of the anatomical cavity via openings on either side of base 91 prior to, during or after a cut is made. When scissor blades 82 and 84 are withdrawn proximally, jaws 18 and 20 can be used as forceps, or as a needle holder or the like. Referring to FIG. 2, tubular shaft 74 is telescopically fitted within the tubular portion of intermediate member 16 and extends through aligned openings in front wall 30, rear wall 31 and intermediate wall 34 of housing 12 to terminate proximally outside housing 12 at spherical reservoir 84 with proximal aperture 88 and stop cock valve 86 lisposed within reservoir 84 for controlling passage of instruments and/or fluids through aperture 88 and into tubular shaft 74.

Handle 90 extends transversely from tubular shaft 74 near the proximal end of tubular shaft 74 and is angled proximally to form a finger rest. Insulated connector 92 can be provided to permit electrical conductors to enter tubular shaft 74 on a side c pposite handle 90 to be connected with electrically conductive elements of instrument 10 for performing unipolar or bipolar electric coagulation, for example using blades 82 and 84 or jaws 18 and 20 as a conductive element. Tubular shaft 74 also carries transverse flange 94 disposed within housing 12 between rear wall 31 and intermediate wall 34 (see FIG. 2). Bias member 100, shown as a helical coil spring, is disposed around tubular shaft 74 and held in compression between flange 94 and intermediate wall 34 to bias inner member 22 proximally within housing 12 and intermediate member 16.

Inner member 22 is prevented from being inadvertently advanced in a distal direction by safety mechanism 36 disposed within the housing 12 as shown in FIG. 2. A push-button type of safety mechanism 36, similar to the one disclosed in the parent application, is shown whereby inner tubular member 22 can be locked in a retracted position with flange 94 abutting rear wall 31 by depressing button 39 and can subsequently be released prior to being moved distally by depressing button 39 a second time. It will be appreciated, however, that other safety mechanisms can be used, including rotatable levers, detents, and splined collars for example. Safety mechanism 36 includes post 37 extending radially through housing 12, bias member 38 connected between post 37 and housing 12 for biasing post 37 radially outward, push-button 39 mounted on top of post 37 externally of housing 12 latch spring 40 disposed within housing 12 for engaging post 37 in a locked position where a lower end of post 37 engages flange 94, and trigger 41 for releasing latch spring 40 to allow post 37 to move radially outward to an unlocked position. Post 37 is oriented transversely relative to the longitudinal axis of inner member 22 and includes annular flange 42 disposed within housing 12. Bias member 38 is shown as a helical coil spring disposed around post 37 and held in tension between housing 12 and annular flange 42 to bias post 37 radially outward of housing 12. Latch spring 40 is formed of a resilient strip of material configured to have flat base 43 secured to an outer wall of the hub and downwardly angled arm 44 extending from a proximal end of base 43 toward the post 37. Arm 44 bends back on itself to form latching surface 45 that is substantially parallel annular flange 42. Transverse extension 46 of arm 44 extends from a distal end of latching surface 45 in parallel to the post 37. Trigger 41 is disposed proximate arm extension 46 and is pivotally mounted in horsing 12. Trigger 41 is generally L-shaped and has leg 49 overlying arm extension 46 and leg 51 extending transversely from leg 49 and at a slight downward angle to be disposed beneath annular flange 42 when post 37 is in the locked position shown in FIG. 2. A torsion spring (not shown) can be connected between trigger 41 and housing 12 to bias trigger 41 in a counterclockwise direction in FIG. 2 such that leg 49 is normally in contact with the arm extension 46.

Referring still to FIG. 2, it will be seen that movable handle 26 is pivotally mounted on pin 102 which is secured to mounting plate 103 that extends outward from side wall 28 along an edge of slotted opening 48. Fixed handle 24 includes finger loop 104 configured to accommodate one or more fingers of the user and shank 106 connecting finger loop 104 with mounting plate 103. Movable handle 26 includes finger loop 110 configured to accommodate one or more fingers of the user and shank 112 connecting finger loop 110 with flattened end portion 114 which extends into housing 12 towards flange 50 of outer member 14 through slotted opening 48. Flange 56 of intermediate member 16 is fixed to housing 12 by bracket 116. As handles 24 and 26 are pressed together, movable handle 26 pivots about pin 102 causing flattened end portion 114 to press flange 50 distally. This causes outer member 14 to move at least partially over cams 70 and 72 thus closing jaws 18 and 20. Note that the surgeon can place fingers through the finger loops or around the finger loops.

A pair of mating protrusions 152 and 154 are carried at opposed locations on finger loops 104 and 110 respectively to lock handles 24 and 26 together when pressed towards one another a predetermined angular distance corresponding to a desired resultant position of jaws 18 and 20. Mating protrusions 152 and 154 are shown having serrated inside surfaces, but can have any other configuration to ratchet, mate frictionally and/or latch together when engaged.

Use of the endoscopic instrument 10 of the present invention is llustrated in FIGS. 10–15, wherein the instrument 10 is shown being guided through portal sleeve 156 positioned in a wall W of an anatomical cavity. Instrument 10 is preferably passed through portal sleeve 156 with jaws 18 and 20 at least partly closed so that instrument 10 can be inserted without catching on anatomical tissue or snagging structure within portal sleeve 156. Since outer member 14 can be held by protrusions 152 and 154 in a position partly closing jaws 18 and 20, the surgeon need not exert any force on the handles of the instrument during insertion.

Figure 10:
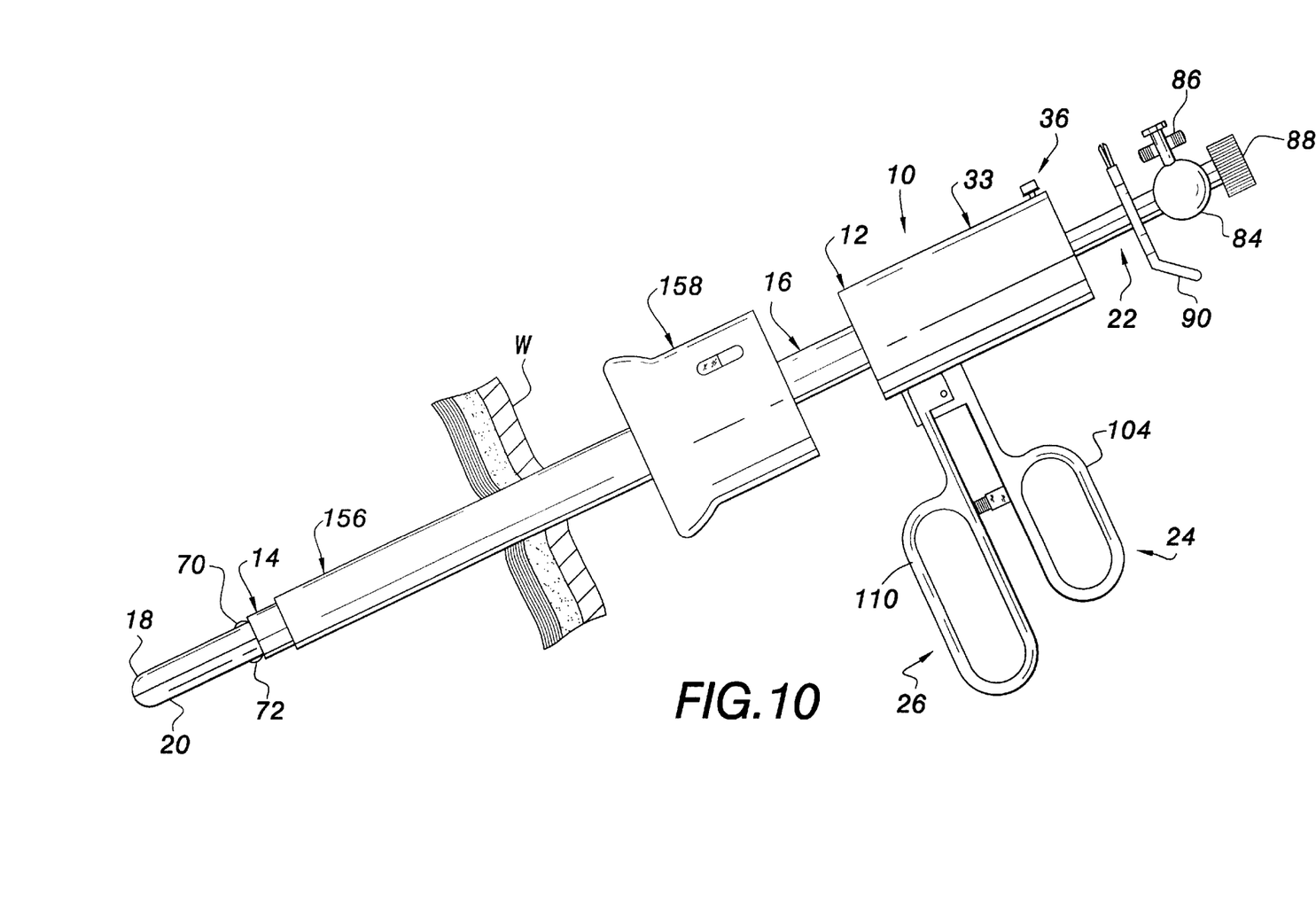
FIG. 10 illustrates the preferred embodiment during use.

With jaws 18 and 20 partly closed, endoscopic instrument 10 is inserted through portal sleeve 156 positioned within the anatomical cavity wall W, as shown in FIG. 10, to access an operative site within the anatomical cavity. Portal sleeve 156 can be positioned in the wall using any suitable penetrating technique, including those creating puncture site by means of removable obturators such as trocars, and is shown carrying valve housing 158 at a proximal end to prevent the loss of pneumoperitoneum during insertion and withdrawal of endoscopic instrument 10. Visualization of the endoscopic procedure can be accomplished using a conventional endoscope (not shown) incorporated into endoscopic instrument 10, for example within tubular shaft 74, or separately positioned within the anatomical cavity through a second portal sleeve located at another puncture site.

Figure 11:
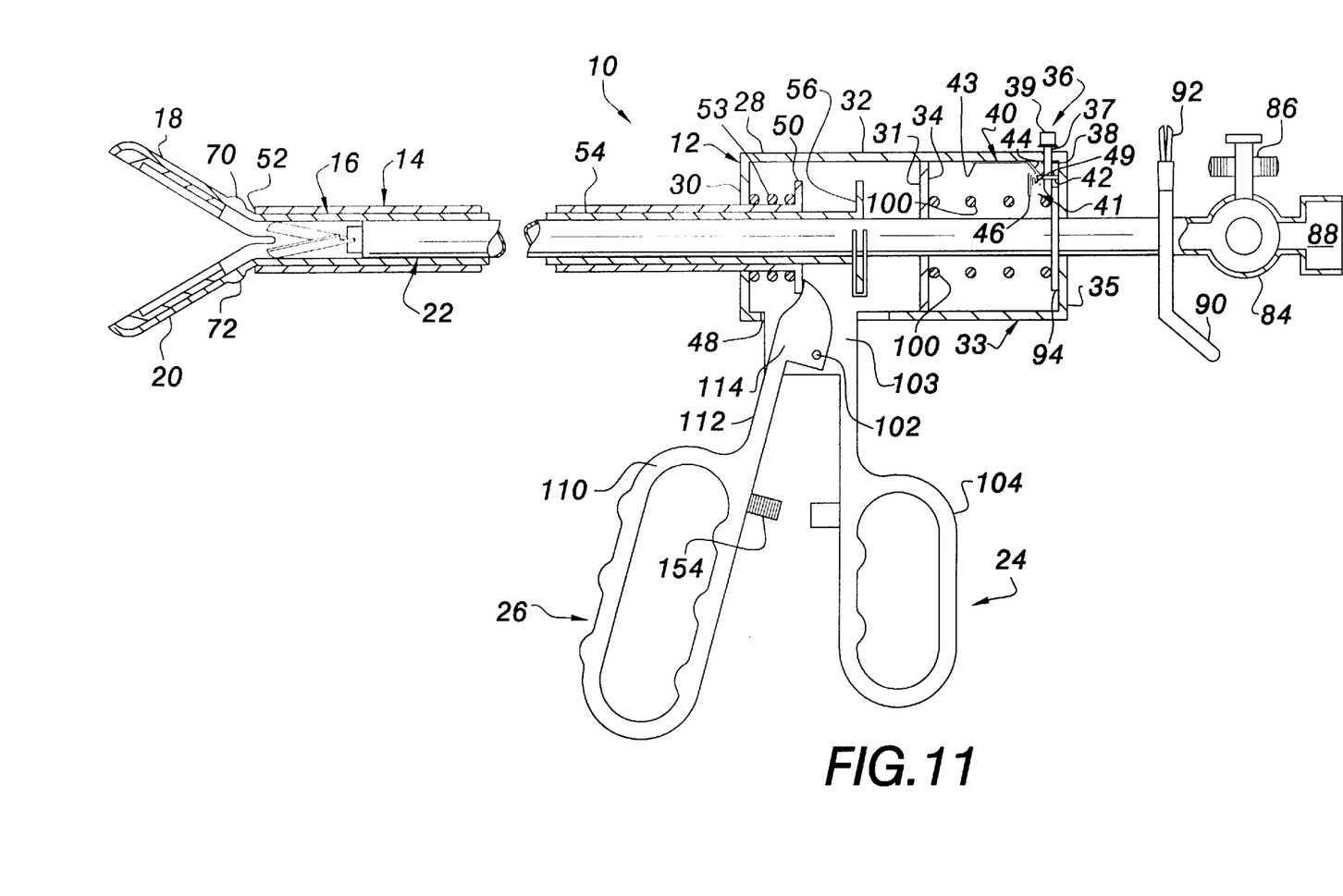
FIG. 11 illustrates the preferred embodiment with the jaws open and the inner member retracted.

Endoscopic instrument 10 is advanced distally through portal sleeve 156 until jaws 18 and 20 emerge into the anatomical cavity. At this point, jaws 18 and 20 can be opened to permit visualization by an endoscope through tubular shaft 74 or can remain closed in the case of using a separately positioned endoscope. If jaws 18 and 20 are to be opened this is accomplished by exerting finger pressure on finger loops 104 and 110 to release protrusion 152 and 154 to spread the loops apart, as shown in FIG. 11 due to the force of biasing member 53. Pivotal movement of finger loop 110 about pin 102 permits flange 50 to move proximally with respect to intermediate member 16. This causes distal end 52 of outer member 14 to slide off cams 70 and 72 in a proximal direction allowing jaws 18 and 20 to spread apart elastically, as illustrated in FIG. 11.

Figure 12:
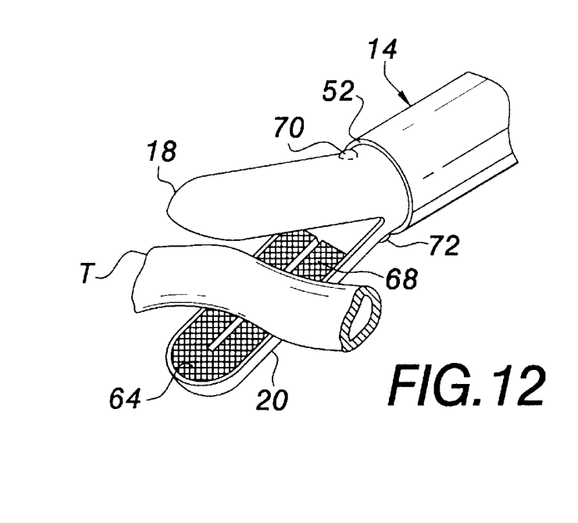
FIG. 12 illustrates the jaws before grasping tissue.
Figure 13:
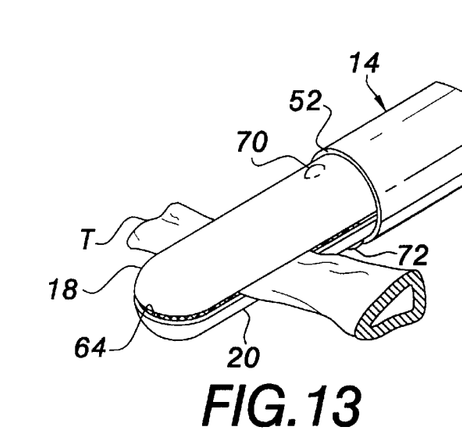
FIG. 13 illustrates the jaws grasping tissue.

Instrument 10 can be moved within the anatomical cavity with jaws 18 and 20 in either the open or closed condition depending on the type of visualization utilized and the desirability of presenting a narrow or wide jaw profile during movement. In FIG. 12 jaws 18 and 20 are shown in the opened condition for being positioned around anatomical tissue T to be grasped. Tissue T is located between tissue grasping inserts 62 and 64 so that when jaws 18 and 20 are partly closed, for example by placing finger pressure on the handles 24 and 26, tissue T will be held securely within the small gap between jaws 18 and 20 for manipulation of tissue T as shown in FIG. 13.

Alternatively, inner member 22 can be advanced prior to closing aws 18 and 20 to permit a cutting operation in the following manner. First, safety mechanism 36 is released by pressing down on push-button 39 to cause annular flange 42 formed on post 37 to engage trigger leg 51 rotating the trigger clockwise in FIG. 2. Trigger 41 is spring-biased in a counterclockwise direction and will thus return to its original position once annular flange 42 advances beyond trigger leg 51. When pressure on the push-button 39 is released, safety bias member 39 will draw post 37 upward in FIG. 2 so that the flange 42 will engage trigger leg 51 from the other side causing the trigger 41 to rotate counterclockwise and trigger leg 49 to bear against arm extension 46. Arm extension 46, and thus latching surface 45, are moved away from the post permitting bias member 38 to move the post to its unlocked position shown in FIG. 14 where the annular flange abuts cylindrical wall 28.

Figure 14:
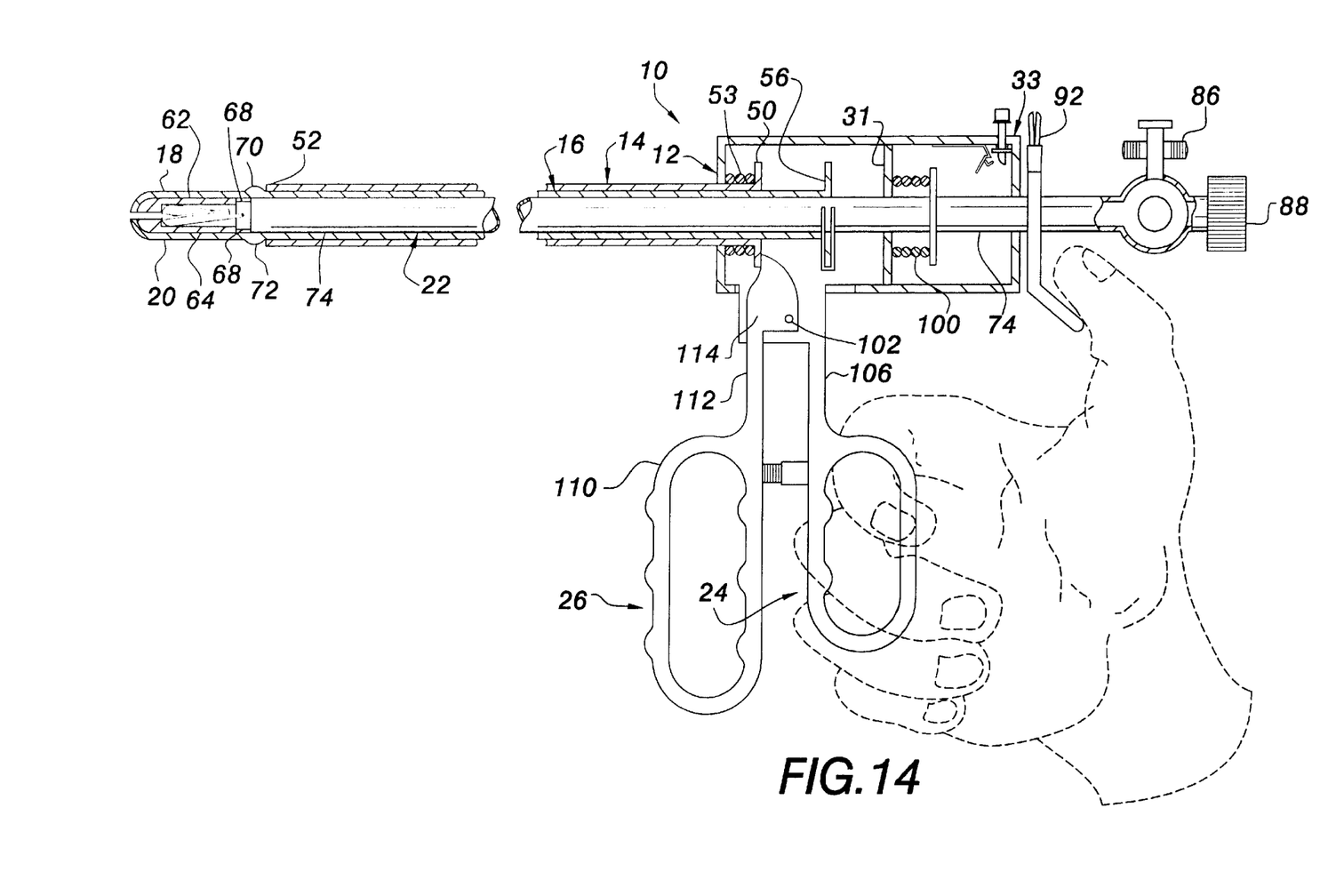
FIG. 14 is a sectional view of the preferred embodiment with the inner member advanced.

With safety 39 mechanism disabled, inner member 22 can be advanced by moving handle 90 toward housing 12. FIG. 14 shows one position of the surgeors hand, in phantom, for accomplishing this task. Blades 82 and 84 at the distal end of the inner member are aligned with grooves 68 formed in jaw inserts 66, for example by use of splines formed along the length of the inner member 22, and are slidable along grooves 68 to be positioned between jaws 18 and 20, when inner member 22 is advanced distally. Since grooves 68 in this embodiment do not extend the entire length of jaws 18 and 20, the distal ends of the grooves 68 can also serve as stops or abutments limiting the distal movement of blades 82 and 84 to permit a distal portion of jaws 18 and 20 to be used for tissue manipulation even when inner member 22 is advanced distally (see FIG. 15). However, grooves 68 can extend the entire length of jaws 18 and 20 to permit blades 82 and 84 to extend entirely across jaws 18 and 20 or even to protrude from a distal end of jaws 18 and 20. Tissue T can be cut completely or partly as desired and will be held between jaws 18 and 20 until the jaws are opened, allowing further procedures, such as cauterization, to be performed with tissue T immobilized. As mentioned previously, tubular shaft 74 is hollow and can thus be utilized for creating suction during the procedure, performing aspiration or irrigation or to facilitate passage of additional instruments or fluids into the anatomical cavity as desired. After a cutting procedure, blades 82 and 84 can be retracted under the influence of bias member 100 or jaws 18 and 20 can be opened to release tissue T and instrument 10 can be manually withdrawn before retracting blades 82 and 84.

Figure 16:
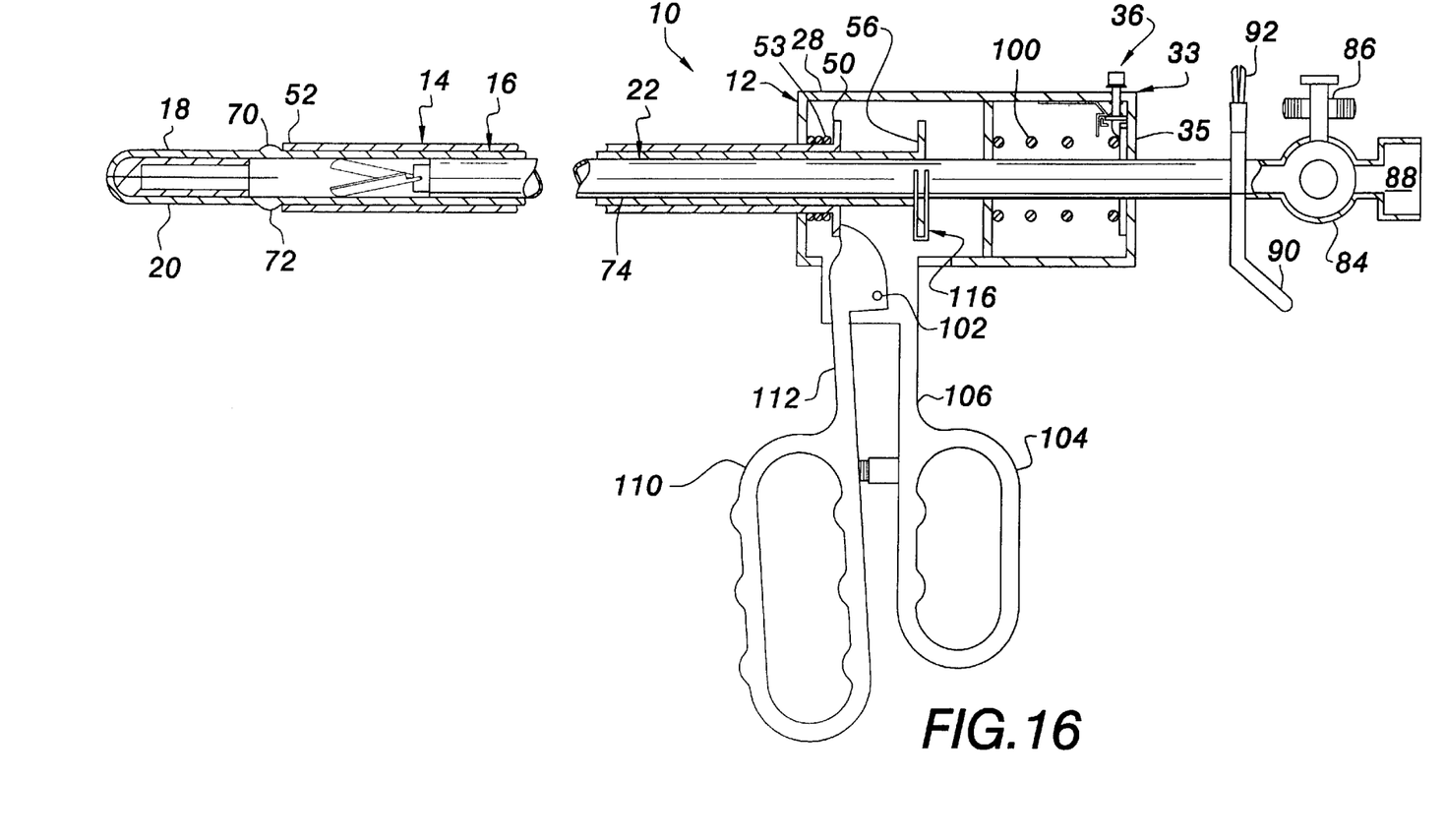
FIG. 16 illustrates the preferred embodiment in section with the jaws pressed tightly together.

As mentioned previously, tissue can be grasped and securely held with jaws 18 and 20 in a partly closed state, i.e. with a gap defined between jaws 18 and 20. However, for certain procedures it may be desirable to draw jaws 18 and 20 completely together as shown in FIG. 16, with or without objects held between the jaws. Jaws 18 and 20 can be closed completely or clamped together by drawing finger loops 104 and 110 towards one another until distal end 52 of outer member 14 slides distally further over cams 70 and 72 to force jaws 18 and 20 into close contact with one another. If tissue or some other object is disposed between jaws 18 and 20, further advancement of outer member 14 over cams 70 and 72 will resul in greater compression of the object. When finger loops 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied.

Figures 17, 18, 19, 20, 21:
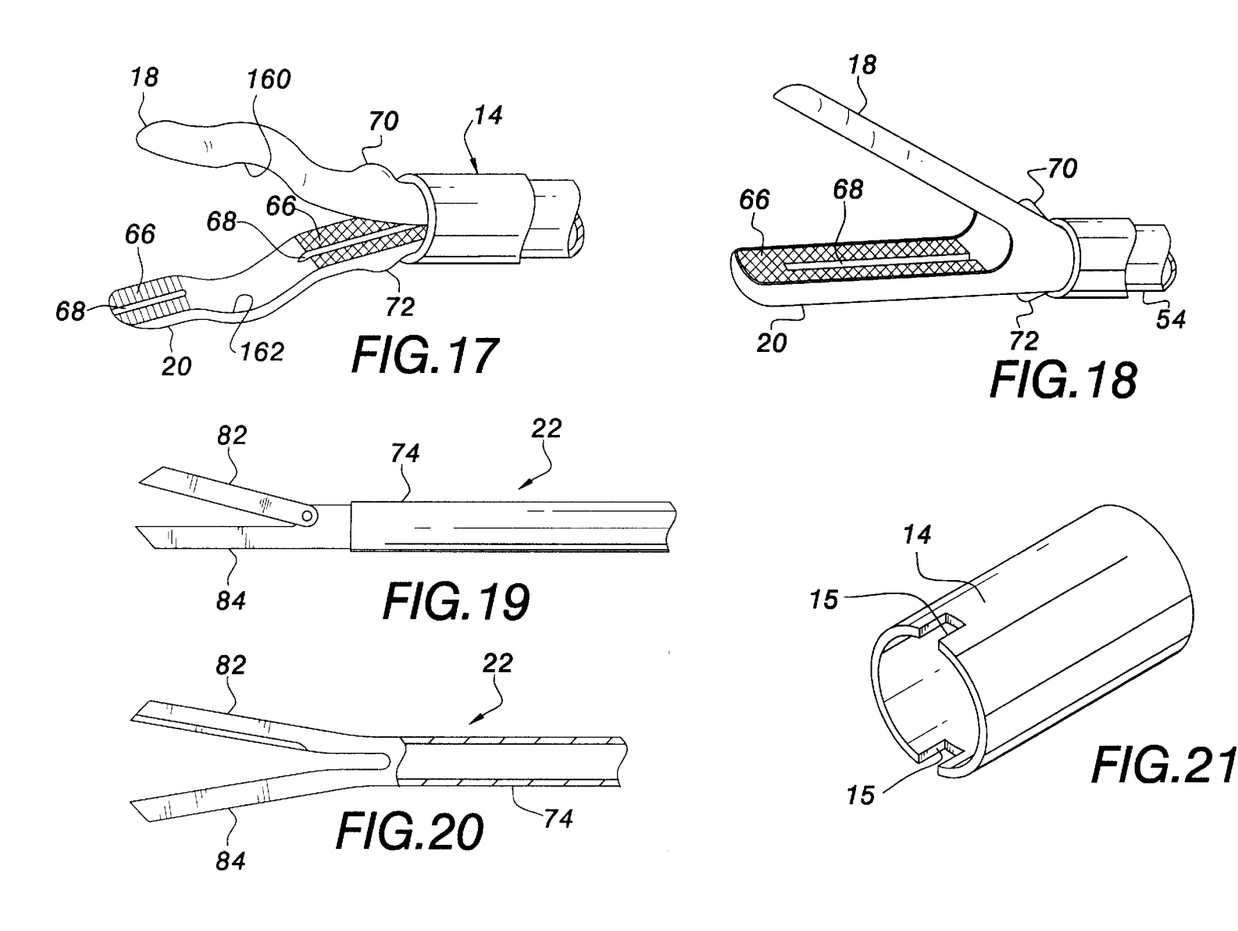
FIG. 17 illustrates a modified set of jaws.
FIG. 18 illustrates another modified set jaws.
FIG. 19 illustrates a modified inner member for use with the jaws of FIG. 18.
FIG. 20 illustrates another modified inner member having integrally formed scissor blades.
FIG. 21 illustrates a modified distal end of the outer member.

FIG. 17 shows further modification of the jaws of endoscopic instrument 10 of the present invention in which jaws 18 and 20 include arcuate or concave portions 160 and 162, respectively, integrally-formed at opposed locations along the length of jaws 18 and 20. Arcuate portions 160 and 162 cooperate to define a substantially circular transverse passage through jaws 18 and 20 when closed and can thus hold a tubular organ, other anatomical tissue or an object therebetween for being manipulated without compressing or flattening the organ, tissue or object. Tissue gripping surfaces 66 are formed on the flat portions of jaws 18 and 20 and can be formed along arcuate portions 160 and 161 as well. Grooves 68 are interrupted by arcuate portions 160 and 162 but extend longitudinally along flat portions of jaws 18 and 20 and are aligned to form is a track for guiding blades 82 and 84 across arcuate portions 160 and 162.

In yet another modification of the jaws of the endoscopic instrument 10 of the present invention, shown in FIG. 18, lower jaw 20 is fixed and extends distally from tubular body 54 along a longitudinal axis of tubular body 54. Upper jaw 18 has cam 70 and s movable from an open position normally extending at an angle relative to the longitudinal axis of tubular body 54 to a closed position where it mates with fixed lower jaw 20. Fixed lower jaw 20 can also carry cam 72. Jaws 18 and 20 include tissue gripping surfaces 66 and grooves 68 formed along the length of the tissue gripping surfaces to serve as a guide for scissor blades 82 and 84. This modification is used in combination with inner member 22 shown in FIG. 19 which includes scissor blades 82 and 84 like those described above but with lower scissor blade 84 being fixed to extend longitudinally and upper scissor blade 82 being pivotally mounted on pin 90 secured to flat base 91 extending distally from tubular shaft 74. Upper blade 82 is biased away from fixed lower blade 84 with a bias member (not shown) and, when fitted within jaws 18 and 20 such as those shown in FIG. 20, is movable toward lower blade 84 by closing jaws 18 and 20 in the manner described above.

FIG. 20 illustrates another modification of the preferred embodiment in which blades 82 and 84 are formed integrally with tubular shaft 74 as a unitary piece. Other elements are similar to the preferred embodiment described above. A distal end of tubular shaft 74 which supports blades 82 and 84, is formed of a suitable resilient material so that blades 82 and 84 can be moved towards and away from each other by jaws 18 and 20. This unitary structure can be applied to the modification illustrated in FIG. 19 also.

FIG. 21 illustrates a modified distal end of outer member 14. Slots 15 are formed in the distal end to receive cams 70 and 72 and thus maintain a proper jaw alignment.

From the above, it will be appreciated that the endoscopic instrument of the present invention permits multiple functions to be performed endoscopically by use of a forceps unit having a tubular member with jaws configured for grasping or holding objects such as anatomical tissue or needles and an inner member telescopically fitted within the forceps unit tubular member and carrying scissor blades that can be selectively placed in the jaws for cutting. The tubular member and jaws of the forceps unit are preferably formed as an integral one-piece construction and are movably disposed within an outer tubular member to permit sliding movement of the outer tubular member over the jaws. The outer member and tubular forceps member can be coupled using any suitable handle mechanism and linkages for producing relative movement between the jaws and the outer tubular member. Because the jaws are carried at the end of a tubular body, the forceps unit can be positioned within an anatomical cavity with the scissor blades being advanced distally through the tubular body for performing cuffing functions. The inner member can also have a hollow tubular shaft open at a distal end for facilitating visualization with a conventional endoscope, illumination with fiber optics or other suitable light sources, for passage of implements such as blades or ligature appliers to cooperate with instruments mounted at the distal end of the inner member tubular shaft, and/or for introducing or collecting fluids prior to, during or after an operative step, such as cutting or puncturing, is completed.

The jaws of the present invention can be straight, curved and/or angled and can have integrally formed or removable inserts with configurations for grasping and holding tissue and object such as needles. Note that, while the jaws are discussed gererally above as part of forceps, the jaws can be used to grasp a needle or other object for suturing or the like. The inserts can have any combination or number of longitudinal grooves formed in the inserts for accommodating additional operating members such as blades, scissors biopsy tools, needles, hooks, surgical clips or any other types of medical implements. The grooves can extend part way to define stops or abutments limiting distal movement of the scissors. The jaws can have any shape in cross-section when closed, including circular, elliptical, rectangular and polygonal configurations, and can have opposed arcuate or concave portions for clamping tubular objects without compressing the objects.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of the electrical connector opposite the handle is merely exemplary of the many various locations at which an electrical connector can be positioned. For example, an electrical connection could be made directly with the housing of the forceps to utilize the forceps jaws as conductive elements for performing electrosurgery. Also, inner surfaces of any of the tubular members can be electrically insulated to permit passage of electrosurgical instruments therethrough.

The handles and linkages shown and described herein for sliding the outer member over the jaws are exemplary of the types of conventional handle mechanisms suitable for performing the function of closing the jaws. However, the handles can have any configuration for producing relative movement between the outer and intermediate members, including two pivoted legs with finger loops and sliding brackets as disclosed in the parent application, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired by selectively disengaging the handles from the jaws.

Suitable linkages include brackets with sliding motion, gears and/or racks mounted on or between handles and the outer and intermediate members, pulleys and cords or any other direct or indirect coupling mechanisms. The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for opposing/releasing the bias member to permit the outer tubular member to be maintained at any position relative to the jaws, for example by frictional engagement.

The components of the endoscopic instrument of the present invention can be made of any suitable medical grade materials to permit sterilization for re-use or for single patient use. The components can be made of multiple parts of various configurations and materials to reduce cost. The instrument can have various valves, stop cocks and seals to control fluid flow therethrough, such as the valve 58 schematically shown in phantom in FIG. 2.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
   a tubular outer member having a proximal end and terminating distally at a distal end;
   an intermediate member having a tubular body disposed telescopically within said outer member, a proximal end and a distal end defining a pair of opposed jaws resiliently biased apart;
   an inner member comprising a shaft and scissor blades at a distal end of said shaft, said inner member being slidably disposed at least partly within said intermediate member;
   a handle coupled with at least one of said intermediate and outer tubular members and configured to move said pair of opposed jaws move between open and closed positions.

2. An instrument as recited in claim 1 wherein said jaws define opposed grasping surfaces.

3. An instrument as recited in claim 2 wherein a longitudinal groove is formed in one of said grasping surfaces.

4. An instrument as recited in claim 3 wherein said longitudinal groove extends part way along said one of said grasping surfaces to define a stop limiting distal movement of said scissor blades advanced along said groove.

5. An instrument as recited in claim 3 wherein said longitudinal groove extends along an entire length of said one of said grasping surfaces.

6. An instrument as recited in claim 2 wherein a longitudinal groove is formed in each of said grasping surfaces.

7. An instrument as recited in claim 6 wherein said longitudinal grooves extend part way along said grasping surfaces to define a pair of stops limiting distal movement of said scissor blades advanced along said grooves.

8. An instrument as recited in claim 6 wherein said longitudinal grooves extend along entire lengths of said grasping surfaces.

9. An instrument as recited in claim 1, further comprising cam members disposed on outer surfaces of said jaws.

10. An instrument as recited in claim 1 wherein said jaws include opposed arcuate portions defining an opening between said jaws.

11. An instrument as recited in claim 1 wherein one of said jaws is fixed parallel to a longitudinal axis of said intermediate member and the other of said jaws is movable.

12. An instrument as recited in claim 1 wherein said scissor blades comprise a pair of pivoted cutting blades with opposed cutting edges.

13. An instrument as recited in claim 12 wherein one of said pivoted cutting blades is fixed to extend longitudinally and the other of said pivoted blades is movable.

14. An instrument as recited in claim 12 wherein both of said pivoted cutting blades are movable.

15. An instrument as recited in claim 1 wherein said scissor blades are integrally formed with said shaft.

16. An instrument as recited in claim 1 wherein a pair of opposed grooves are formed in said jaws and said scissor blades are biased apart to fit within said grooves when said inner member is advanced to place said scissor blades between said jaws.

17. An instrument as recited in claim 1 wherein sail inner member is biased proximally relative to said intermediate member, said instrument further comprising a handle mounted on said inner member for being advanced distally.

18. An instrument as recited in claim 17 further comprising;
   safety means for locking said inner member to prevent movement of said inner member relative to said intermediate member.

19. An instrument as recited in claim 1 wherein said inner member includes valve means at a proximal end for controlling passage through said inner member.

20. A method of performing surgical procedures comprising the steps of
   introducing a tubular member with jaws through an opening in an anatomical cavity wall;
   advancing an inner member having scissor blades distally through the tubular member so that said scissor blades are between said jaws; and
   performing a cutting procedure with said scissor blades.

21. A method as recited in claim 20, further comprising before said advancing step, grasping and manipulating tissue with said jaws.

22. A method as recited in claim 21 wherein said introducing step includes closing said jaws by sliding an outer tubular member over the jaws.

23. A method as recited in claim 22 wherein said grasping step includes sliding said outer tubular member proximally with respect to said jaws to permit said jaws to resiliently separate, positioning the anatomical tissue between said jaws and sliding said outer tubular member distally towards said jaws to close said jaws around the anatomical tissue.

24. A surgical instrument comprising
   a tubular outer member having a proximal end and terminating distally at a distal end, a channel being defined through said outer member;
   an intermediate member having a body disposed at least partly within said outer member, a proximal end and a distal end defining a pair of opposed jaws resiliently biased apart;
   an inner member comprising a shaft and scissor blades at a distal end of said shaft, said inner member being slidably disposed at least partly within said channel;
   a handle means coupled with at least one of said jaws and configured to move said jaws between open and closed positions.

25. An instrument as recited in claim 24 wherein said channel passes through said intermediate member.

* * * * *